United States Patent [19]
Storace

[11] Patent Number: 5,290,304
[45] Date of Patent: Mar. 1, 1994

[54] TROCAR SYSTEM

[75] Inventor: Anthony Storace, Norwalk, Conn.

[73] Assignees: Ingram S. Chodorow, Saddle River, N.J.; Myron S. Blatt, Chappaqua, N.Y.; a part interest to each

[21] Appl. No.: 699,722

[22] Filed: May 19, 1991

[51] Int. Cl.[5] .............................................. A61B 17/32
[52] U.S. Cl. ................................... 606/184; 604/164; 30/366
[58] Field of Search ............... 604/110, 160, 161, 164, 604/165, 168, 169, 185, 188, 246, 247, 248, 264, 272, 274, 283; 606/184, 185; 128/751–754; 30/151, 152, 162, 366, 367, 368

[56] References Cited

U.S. PATENT DOCUMENTS

| | | | |
|---|---|---|---|
| 4,411,653 | 10/1983 | Razi | 606/185 |
| 4,535,773 | 8/1985 | Yoon. | |
| 4,601,710 | 7/1986 | Moll et al. | |
| 4,654,030 | 3/1987 | Moll et al. | |
| 4,902,280 | 2/1990 | Lander. | |
| 5,116,353 | 5/1992 | Green | 606/184 |
| 5,152,754 | 10/1992 | Plyley et al. | |

Primary Examiner—C. Fred Rosenbaum
Assistant Examiner—W. Lewis
Attorney, Agent, or Firm—Michael J. DeSha

[57] ABSTRACT

A trocar system comprises a trocar housing, a pointed stylet arranged so that the pointed tip can be selectively extended outwardly (distally) from the trocar housing, a return spring in the trocar housing for retracting the stylet into the housing and a piston and piston latch system disposed within the trocar housing for restraining the stylet from retracting. The piston includes a cam element for de-latching the piston from its latched position to allow the return spring to retract the piston into the housing. The stylet engages the piston in a slot to permit limited longitudinal movement of the stylet into the housing. A distally-biased element which carries an engaging pin and is forced to move proximally by the tissue resistance experienced as the trocar is forced to puncture a body cavity wall, automatically moves to its original distal location after the tip of the trocar has completely passed through the wall. The sequence of movements, first proximal and then distal, automatically first arm and then trigger the de-latching mechanism which enables the return spring to retract the pointed stylet into a protective housing.

19 Claims, 11 Drawing Sheets

TROCAR SYSTEM

FIELD OF THE INVENTION

The invention relates to a trocar and more particularly to a trocar of the type having a protective tube for covering the tip of the trocar to prevent injury through inadvertent contact.

BACKGROUND OF THE INVENTION

Trocars are well known surgical devices. A trocar comprises a stylet, that is, a pointed implement for penetrating a body cavity wall, and associated parts which are surrounded by a tube or cannula which follows the stylet into the cavity and stays in place after the stylet and other associated parts are removed. The combination of trocar and cannula will be referred to herein as a trocar system.

It is known to position protective tubes over the pointed end of the stylet to protect patients and surgeons from injury through inadvertent contact with the sharp tip. Such a tube is described, for example, in U.S. Pat. No. 4,902,280. In this reference, a concentric protective tube is slidably spring biased to fully cover the pointed end. In use, the protective tube moves proximally to expose the pointed end to allow it to puncture the cavity wall. After the pointed end of the stylet and the protective tube pass fully through the wall, the protective tube is able to slide distally under the force of the spring to again cover the pointed end of the stylet to prevent tissue injury.

U.S. Pat. No. 4,535,773 describes an invention wherein the pointed end of a stylet, which protrudes from a protective housing for the purpose of puncturing tissue, also carries pressure sensors which signal the reduction of pressure accompanying full passage through the body wall. This signal causes a solenoid, located within the housing, to become energized and thereby disable a detent which holds the stylet in an extended position, thus allowing a pre-tensioned spring to pull the stylet into the housing.

Although from this cited art it is known to shield the pointed end after the concentric tube has fully passed through the cavity wall, it has now been found to be preferable to invoke protection of the sharp tip at an earlier time, prior to the concentric tube entering or passing through the puncture hole in the process of puncturing the cavity wall in order to further reduce the probability of inadvertently injuring internal tissue. U.S. Pat. No. 4,902,980 requires that the tube fully project through the hole in order to invoke the protective features. Further, while the retraction of the stylet within the housing, as described in U.S. Pat. No. 4,535,773, does improve the level of protection, the impracticality of providing pressure sensors on the stylet and the unreliability of solenoids together with the need to provide electrical power along with the associated costs of these additional parts combine to make this approach impractical.

SUMMARY OF THE INVENTION

Accordingly, it is an object of the invention to provide a trocar system in which the protection of the point is reliably invoked as soon as the point passes through the cavity wall.

It is a further object of the invention to shield the pointed end of the stylet at all times prior to actual use.

An additional object of the invention is to accomplish shielding of the stylet point by having the stylet withdraw into a protective housing using a simple, low-cost, reliable mechanical apparatus.

In accordance with the invention, there is provided a two part trocar system. One part (the trocar) comprises a trocar housing, a pointed stylet arranged so that the pointed tip can be selectively extended outwardly (distally) from the trocar housing, a return spring in the trocar housing for retracting the stylet into the housing and a piston and piston latch system disposed within the trocar housing for restraining the stylet from retracting. The piston includes a cam element, preferably flexibly attached to the body of the piston, for de-latching the piston from its latched position to allow the return spring to retract the piston into the housing. The stylet engages the piston in a slot to permit limited longitudinal movement of the stylet into the housing. The piston is arranged such that it is in a proximal position prior to the use of the trocar, with the stylet fully retracted within the first housing. The stylet is biased distally, preferably by a second spring located within the trocar housing. A set link button operable upon the piston protrudes from the proximal end of the housing so as to be depressed by the surgeon as force is applied to the trocar housing in the normal course of establishing a puncture site by driving the trocar through the tissue of the body cavity wall.

The second part of the trocar system comprises a second housing which is located coaxially to the trocar housing and which cooperates with the trocar housing to define a handgrip and an extension of the second housing known as a cannula surrounding the trocar. The second housing includes in known manner a seal through which the first housing slides in a gas-tight manner. The seal includes the serial placement of an O-ring for sealing against the body of the first housing and a flap valve which covers the O-ring when the first housing is removed.

Prior to use, the set link button is in its extended condition and the stylet is retracted within the first housing. Preferably, the surgeon grips the trocar system with its proximal end against the palm and the fingers are wrapped around the taper of the second housing.

In use, the distal end of the cannula, which is open to passage of the stylet, is pressed against the body cavity wall. Depression of the set link button while the first housing is forced against the cavity wall advances the piston system progressively in the distal direction until the piston is latched in a predetermined distal location within the trocar housing and the return spring is compressed against the distal end of the piston. In this state, the stylet, whose end now protrudes beyond the trocar housing, is restrained against retraction into the housing, preferably by a pin extending lateral to the stylet longitudinal axis, which pin bears against the proximal end of the piston slot through the action of the second spring. The pin and slot thus define the limits of travel of the stylet relative to the piston which is selectably latched to the trocar housing by the piston latch system.

Further advance of the trocar system causes the sharp end of the trocar stylet to puncture the tissue of the cavity wall. When the pointed end breaks through the inner surface of the wall, the longitudinal force on the stylet point drops nearly to zero. In this condition, the stylet is moved distally by the second spring from the proximal toward the distal end of the piston slot. In so doing the stylet de-latches the piston which is then driven by the pre-loaded first spring to retract the stylet into the cannula housing to thereby shield the point. The pre-load force in the first spring exceeds that of the second spring by an amount sufficient to allow the foregoing to occur as described.

In one preferred embodiment, the de-latching occurs as the stylet pin engages a cam element flexibly attached to the piston that carries an abutting edge for engagement against the retention link which is flexibly attached to the trocar housing.

In another embodiment, the piston rotates as the stylet pin moves first proximally and then distally with the stylet; such rotation aligns slots in the piston with restraining edges on the trocar housing. When the piston is so aligned, it is no longer restrained and can retract the stylet.

In yet another embodiment, the pin for delatching the piston is carried on an inner surface of a distally biased tubular slideable shield. Distal movement of the shield carrying the pin causes the retaining link to disengage from the piston to retract the stylet.

The cannula of the second housing, being close in diameter to the pointed end of the trocar, follows the trocar point into the body cavity and remains in place when the trocar housing containing the stylet is removed from the second housing thereby leaving the cannula extension of the second housing in place within the puncture.

BRIEF DESCRIPTION OF THE DRAWINGS

These and other objects and advantages of the invention will become more apparent from the following description in conjunction with the accompanying drawing wherein.

DETAILED DESCRIPTION OF THE PREFERRED EMBODIMENTS

Figure 1:
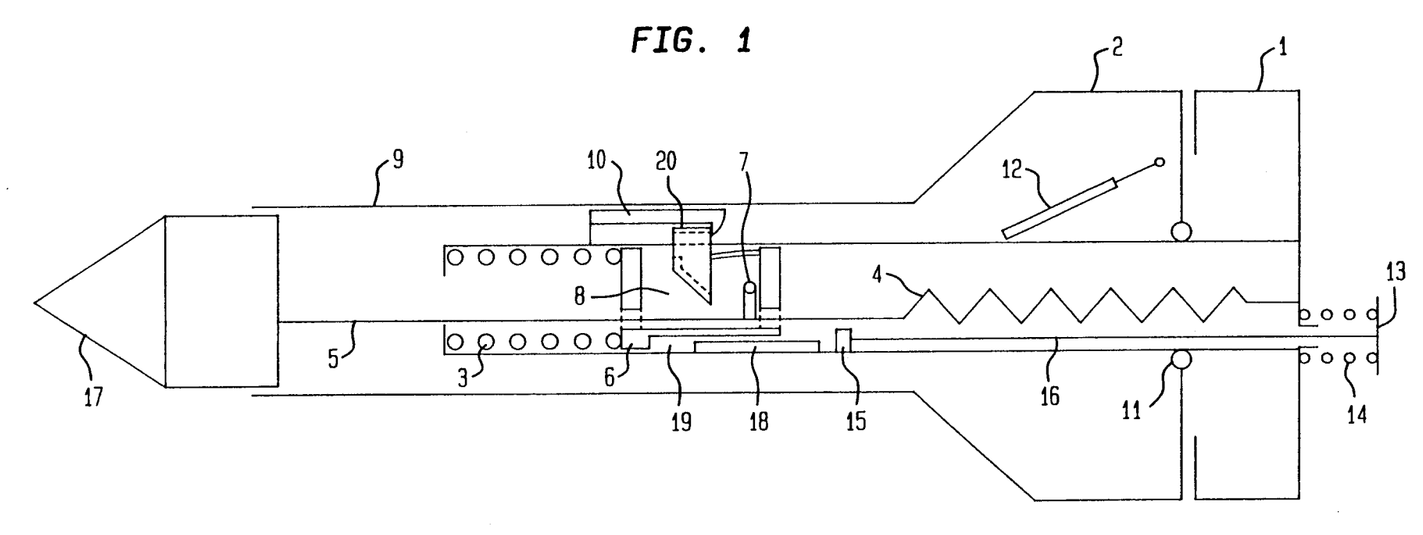
FIG. 1 illustrates the trocar system in accordance with the invention.

FIG. 1 shows an overall view of a trocar system in accordance with the invention. Trocar housing 1 is slideably disposed within an outer housing shown at 2 concentric with housing 1. Return spring 3, preferably a concentric spring as illustrated, is arranged against an abutment edge of the trocar housing 1. Second spring 4 is connected between the trocar housing 1 and stylet 5. The other end of spring 3 is fitted against piston 6 which is slidingly mounted within housing 1 and through the interior of which the stylet 5 also passes.

Stylet pin 7 is shown mounted on stylet 5 and is captured in a slot 8 of piston 6. The housing 2 extends to the left in the illustration (distally) to form a tube or cannula 9 whose inner diameter is preferably only slightly larger than the diameter of the largest cross-section of the end of the stylet. Retention link 10 which will be described more fully below in connection with FIG. 7E is mounted on housing 1 and enables the selective latching of piston 6 to housing 1.

A gas-tight seal is provided in conventional manner by O-ring 11 and flap valve 12 between housing and housing 2. See, for example, U.S. Pat. No. 4,902,280. Set button 13 is mounted on first housing 1 by set link spring 14 which is normally in an uncompressed state, but which is shown in this illustration in its compressed state. Movement of the set button 13 is communicated to piston 6 through set link tip 15 abutting piston 6 at the end of the set link flexure rod 16. Set cam 18 is arranged to control the movement of the set link tip 15 as the piston 6 moves in the distal direction. The stylet 5 terminates at the distal end in a sharp tip 17. In a preferred embodiment, piston 6 has a slot 19 described more completely in relation to the discussion of the setting mechanism in FIGS. 7A through 7F.

Stylet pin 7 is shown at the extreme proximal limit of its travel within piston slot 8. In this state, force applied to the stylet tip 17 is transferred to the piston 6 by stylet pin 7 bearing against the end of piston slot 8. The piston 6 in turn transmits the force to retention link 10 attached to the trocar housing, the proximal end of which will conveniently rest in the surgeon's hand.

Figure 2:
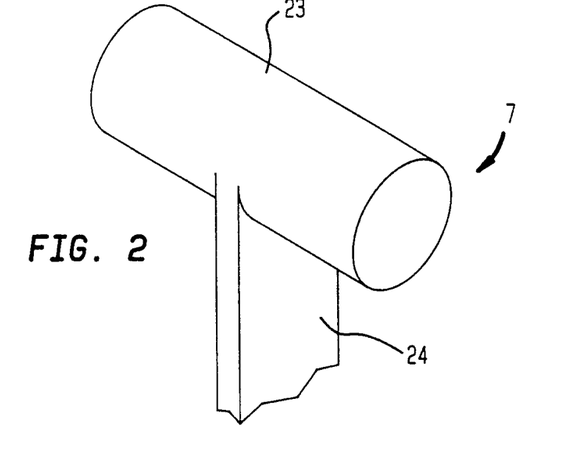
FIG. 2 is a schematic view of the stylet pin.
Figure 3:
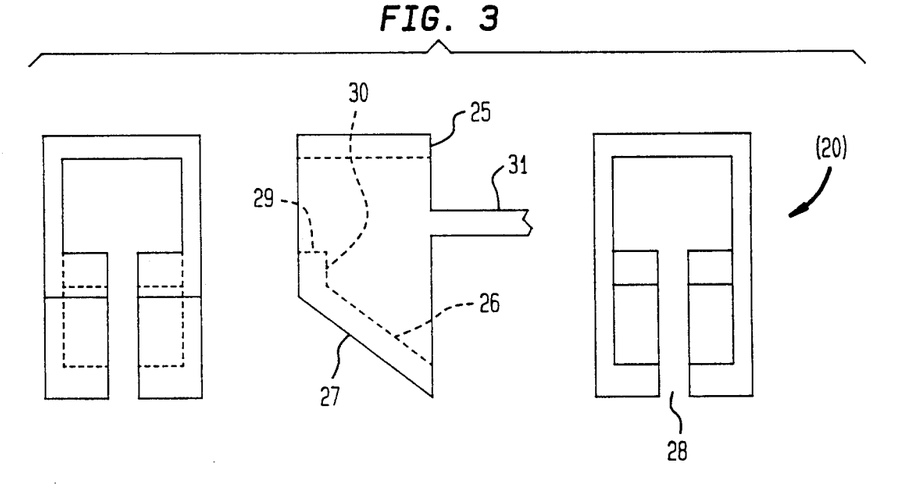
FIG. 3 is a schematic view of the flex cam arrangement.

The piston 6 is selectably latched to trocar housing 1 when it is moved to a predetermined position by the engagement of flex cam element 20 with retention link 10 on housing 1. A preferred embodiment of stylet pin 7 that will enable de-latching of the piston 6 from retention link 10 is shown in FIG. 2. The preferred embodiment of corresponding cam element 20 is shown in FIG. 3.

FIG. 2 illustrates details of stylet pin 7, cylindrical cam driver 23 and rectangular stud section 24. FIG. 3 shows the corresponding features of flex cam element 20. Pin 7 interacts with flex cam element 20 to effect de-latching of the piston 6.

Flex cam element 20 comprises abutment edge 25, release ramp 26, return ramp 27, rectangular slot 28, reset edge 29, ramp stop 30, and flex cam support 31. Ramp 26 is slightly wider than driver 23 to allow the driver entry while slot 28 is slightly wider than stud 24 in order to allow the stud 24 to pass while driver 23 impinges on ramp 26. Edge 25 abuts the lip of retention link 10 which restrains piston 6 to which element 20 is attached. Ramp stop 30 provides a temporary resting place for pin 7 wherein element 20 is held in a partially deflected position until piston 6 has moved a predetermined distance from its latched position. This feature assures that element 20 will properly de-latch from link 10 rather than possibly re-latching due to element 20 bouncing and rebounding to re-latch link 10 before piston 6 has had a chance to be released.

It will be understood that other methods of latching and de-latching will occur to those skilled in the art. For example, the slot in piston 6 could be a curved slot so that the piston is rotated by the travel of the stylet 5 in order to effect the release of the latch. Additionally in this case, the stylet is required to be independently constrained to move in a linear manner. It will be appreciated that the latch in this case could also be a feature of the piston as opposed to the flex cam element previously described.

Figure 4:
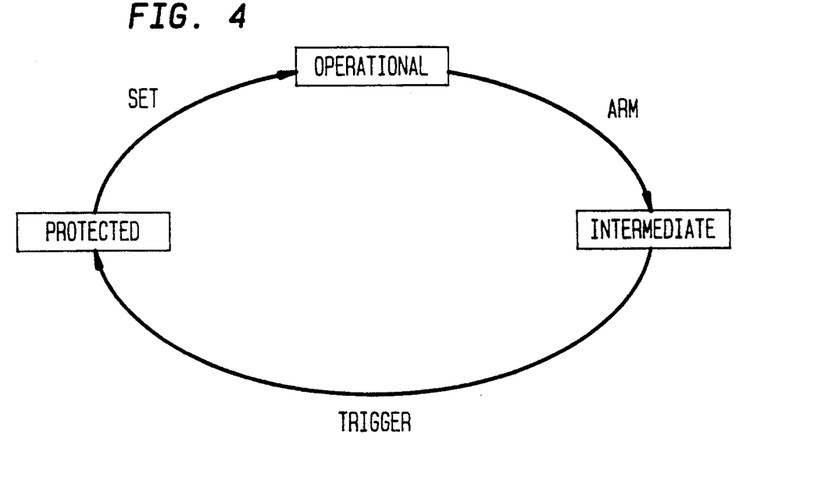
FIG. 4 illustrates the logical sequence of the states and processes in the device in accordance with the invention.

For a better understanding of the operation of the trocar in accordance with the invention, FIG. 4 illustrates the logical sequence of states and processes through which the instrument will pass. It should be understood that the operations described are essentially merged and are separated here for ease of discussion.

The trocar device in accordance with the invention can be placed in any one of three states. The "operational" state as defined herein is a state where the pointed stylet tip extends beyond the open end of the trocar housing and is ready to be pressed against the surface of the tissue to be punctured. The operational state is achieved through the "set" process. This is the process wherein the stylet is extended from its retracted position within the trocar housing to a distal position where its sharp point is exposed. In accordance with the invention, at the end of this process, when the trocar is in its operational state, the piston is latched in its position.

In the "intermediate" state, the stylet is partially retracted into the trocar housing with the tip still being extended to a degree dependent upon the amount of force being exerted against the point of the stylet. It will be appreciated that in this state, the trocar may still be used to puncture the wall of the body cavity. This "intermediate" state is reached in the "arm" process as longitudinal force is applied to the pointed end of the stylet.

In the "protected" state, the stylet has been fully retracted within the trocar housing and cannot be used to puncture the wall of a body cavity. This state is achieved by the "trigger" process wherein the piston is de-latched and retracts the stylet from its operational position.

In FIG. 1, the trocar system is illustrated in the intermediate state where longitudinal force applied to the stylet tip 17 forces stylet 5 to partially retract into trocar housing 1. Such retraction proceeds as long as the longitudinal stylet tip force exceeds the resisting force in second spring 4 and until stylet pin 7 reaches the extreme proximal end of piston slot 8, the position shown in FIG. 1. When stylet pin 7 reaches the end of piston slot 8, it bears against the wall of piston slot 8 which bearing transfers further force applied to the stylet tip directly to piston 6 which is latched to housing 1 by the engagement of the lip of retention link 10, flexibly attached to housing 1, with abutment edge 25 of flex cam element 20.

For proper operation of the illustrated embodiment, it is important to note that the longitudinal force required to be applied to stylet tip 17 to force stylet 5 to retract to the point where stylet pin 7 contacts the proximal end of piston slot 8 be less than the force required to force stylet 5 to fully pierce the tissue. This is so because such partial retraction of stylet 5 to the above described condition in effect arms the instrument for the full retraction of stylet 5 into housing 1. Such full retraction is triggered by the reduction of force on stylet tip 17. This aspect ca be better understood by reference to FIG. 5.

Figure 5:
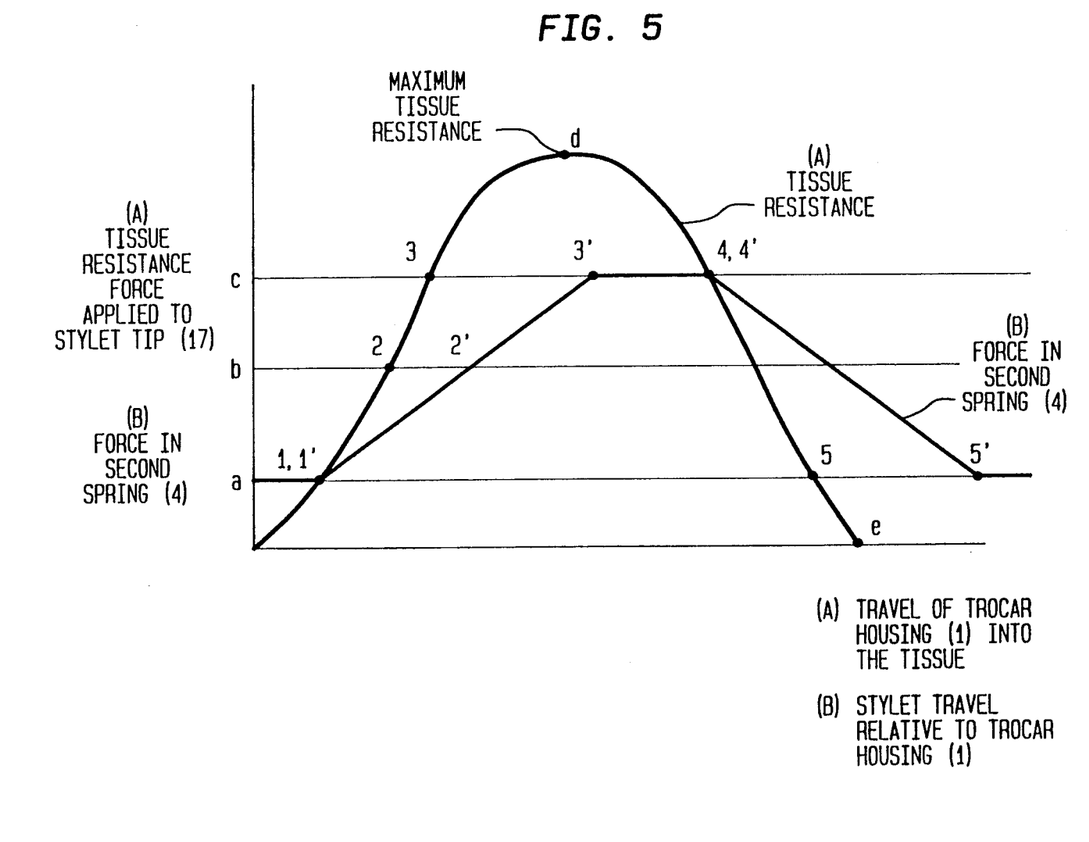
FIG. 5 illustrates the force relationships involved in the process of puncturing a representative body cavity wall.

Referring to FIG. 5 and as required to FIG. 1, the curve labeled "tissue resistance" in FIG. 5 is to be read according to the legends labeled (A) while the curve labeled "force in second spring 4" is to be read according to the legends labeled (B). The points (a) and (c) describe the force levels of second spring 4 corresponding to stylet pin 7 extreme locations within piston slot 8. Point (a) represents the force at the most distal end of the slot 8 where the spring is compressed least while point (c) represents the force at the most proximal end where the spring is compressed the most. It will also be appreciated that points a, b, and c also represent tissue resistance levels which will be experienced as trocar system punctures the tissue wall. Points 1 through 5 represent specific combinations of tissue resistance and trocar system travel while points 1' through 5' represent specific combinations of second spring 4 resistance force and travel of stylet pin 7 within piston slot 8.

As seen from this FIG. 5, the tissue resistance force applied to stylet tip 17 will be zero until set button 13 is depressed. As set button 13 is depressed, with the trocar system pressed against the tissue, stylet tip 17 begins to contact tissue as it emerges from the housing 1. As the tip emerges, tissue resistance rises and as stylet pin 7 moves in response from the distal end to the proximal end of slot 8 of piston 6, second spring 4 is compressed further from its initial state to a shorter length. It will be understood that second spring 4, being a compression spring and therefore applying distal force to stylet 5, experiences an increase in its spring force level in the process. Such increase continues until stylet pin 7 contacts the proximal end of piston slot 8 which prevents further compression of the second spring 4.

Thus, to the left of point 1,1' the pre-load in spring 4, shown at (a) in FIG. 5, exceeds the tissue resistance and therefore stylet 5 remains at the distal end of slot 8. At point 1,1', tissue resistance is equal to the pre-load in spring 4,(a). As tissue resistance rises above (a), the stylet 5 begins to move away from the distal end towards the proximal end of the trocar. This movement is illustrated by the line from point 1,1' to point 3'. The horizontal distance between these points (read according to legend B) is equal to the full travel of stylet pin 7 in slot 8. The corresponding vertical distance is equal to the increase in the force of spring 4 due to its further compression. The increase is determined by the travel allowed by slot 8 and the spring constant of spring 4.

It will be appreciated that it is desirable to keep this force increase low because proper functioning of the instrument requires that tissue resistance exceed the maximum force in spring 4. Thus, for example, if the force at point c is allowed to rise higher than at point d, which is the peak tissue resistance force experienced during the puncture operation, the instrument may fail to operate properly. It will be noted that this may happen in two general ways. First if the travel allowed by the slot 8 is too large or if the spring constant is too large, then point c may be higher than point d. Conversely, though, if the tissue to be punctured is extremely thin, maximum tissue resistance, represented by point d may be less than point c. In either case, stylet pin 7 may fail to traverse the full length of slot 8 and result in a failure to arm the trocar system.

Similarly, it will be understood that it is necessary to correctly determine the point (a). If the selected pre-load force in spring 4, represented at (a), is too low, stylet 5 may properly move from the distal to the proximal end of slot 8, but may fail to return when tissue resistance falls upon the completion of the puncture, represented in FIG. 5 by curve (A) between points d and e. This failure of stylet pin 7 to return from the proximal end to the distal end of slot 8 may result in a failure t trigger the release of piston 6 and result in a failure to completely retract stylet 5 into housing 1.

It will be appreciated that the resistance to distalward movement exists in the cam interaction of pin 7 with release ramp 26 of flex cam element 20. Thus the preload of spring 4 must exceed the sum of such resistance and the sliding frictional resistance exerted on stylet 5 through its contact with other parts of the trocar system.

Point 2 represents an intermediate tissue resistance of (b) with an equal force in spring 4 at point 2'. Point 2' represents a position of stylet pin 7 intermediate between its extreme distal and proximal positions within slot 8.

Beyond point (d), tissue resistance falls continuously to point (e), which point is representative of substantially zero force. At point 4,4' tissue resistance again equals the maximum force in spring 4, (c), similar to that at point 1,1'. Beyond point 4,4', stylet 5 progressively returns to its distalmost location within slot 8 along the line from point 4,4' to point 5'. At 5' stylet pin 7 is again resting against the distal end of slot 8. In returning from the proximal to the distal end of slot 8, stylet pin 7 cams down flex cam element 20 out of engagement with retention link 10 to release piston 6 which results in the retraction of stylet 5 within housing 1. This process is referred to herein as "triggering", while the complementary travel from the distal to the proximal end of slot 8 is referred to herein as "arming" of trocar system release.

The distal advance of the stylet which releases the piston must be made small in order to further reduce the probability of injury to the internal organs as the stylet tip breaks through the wall of the cavity.

Figure 6A:
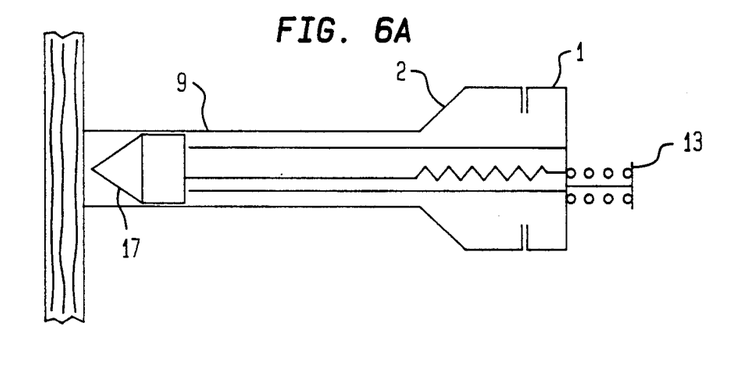
FIGS. 6A through 6D show in sequential diagrammatic cross-sectional views an embodiment of the present invention in use in puncturing a body cavity wall.
Figure 6B:
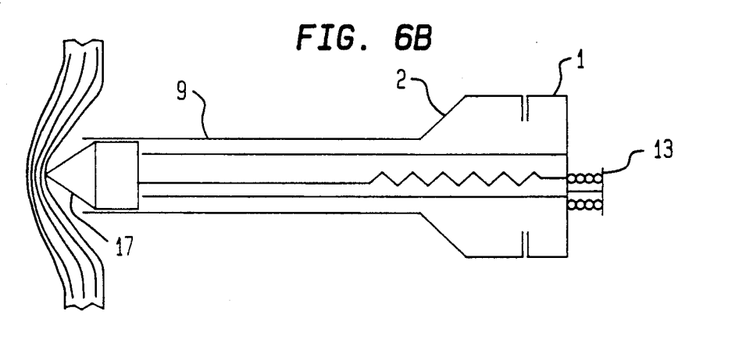
Figure 6C:
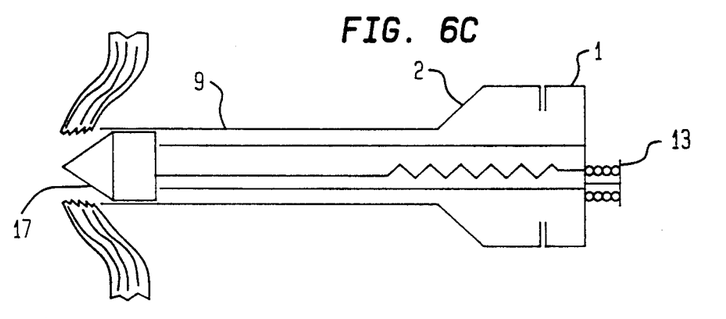
Figure 6D:
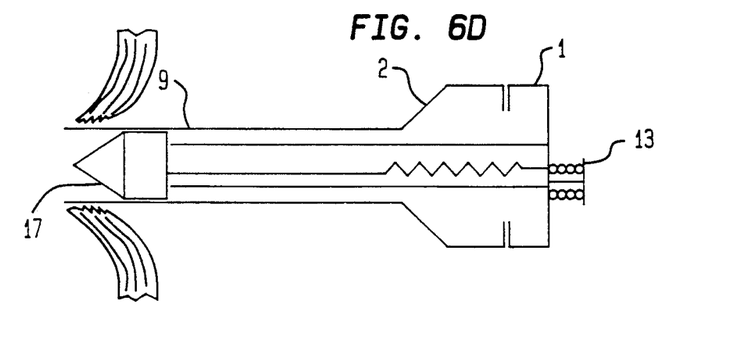

FIGS. 6A through 6D illustrate the normal sequence in utilization of the trocar system. In FIG. 6A, the trocar system is shown pressed against the tissue to be punctured. In FIG. 6B, set button 13 is depressed to advance the stylet 5 from its retracted position within the housing 1 to its distal extended position and entering the tissue. FIG. 6C shows stylet 5 breaking through the wall of tissue with cannula 9 following. In this condition, stylet 5 is free of tissue resistance and is ready to be retracted automatically into housing 1. Cannula 9 is desireably close in diameter to the diameter of stylet tip 17, and therefore may easily be forced through the opening created by stylet tip 17. FIG. 6D shows cannula 9 within the puncture site established by stylet tip 17.

Referring now to FIGS. 7A through 7E, the operation of an embodiment of the setting system in accordance with the invention will be described. The trocar system is placed in the operational state by depressing set button 13 (FIG. 1). As seen in FIGS. 7A through 7F, set cam 18 is arranged on the internal surface of housing 1. As set button 13 is depressed, set link tip 15 which is connected to set button 13 through flexible set link flexure rod 16, advances piston 6 within housing 1 in the distal direction.

Figure 7A:
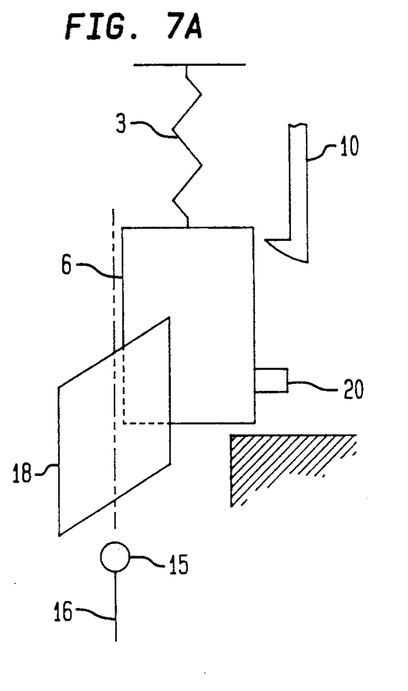
FIGS. 7A-7F illustrate a schematic view of the setting arrangement for converting the instrument from the protected state to the operational state.
Figure 7B:
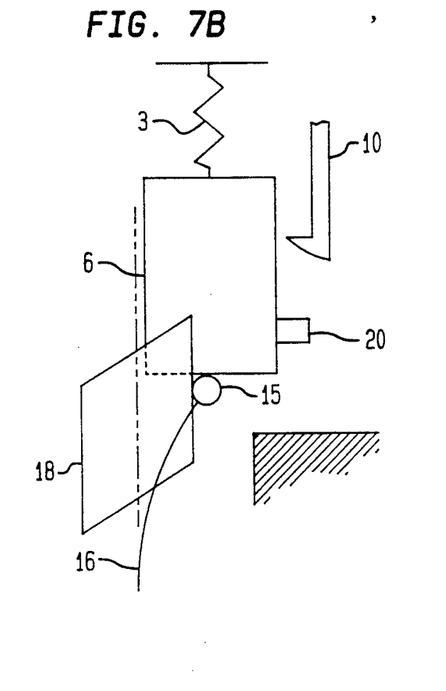
Figure 7C:
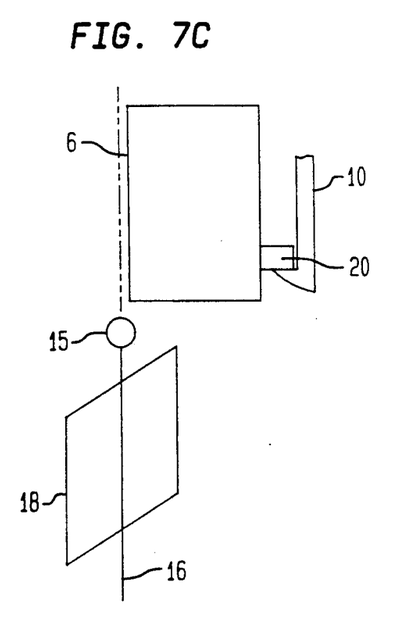
Figure 7D:
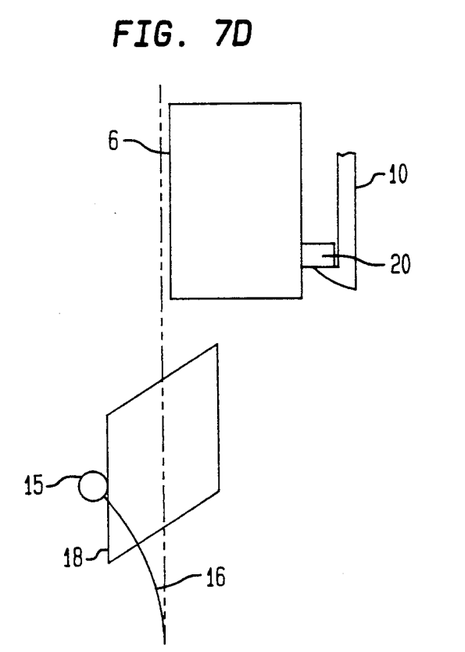
Figure 7E:
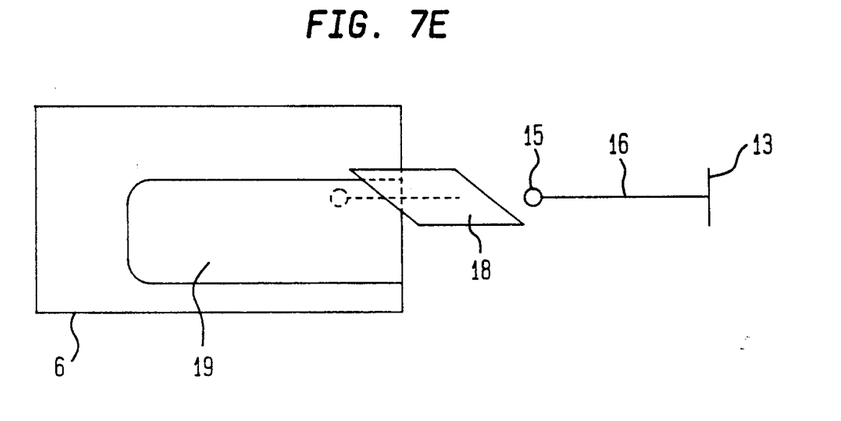
Figure 7F:
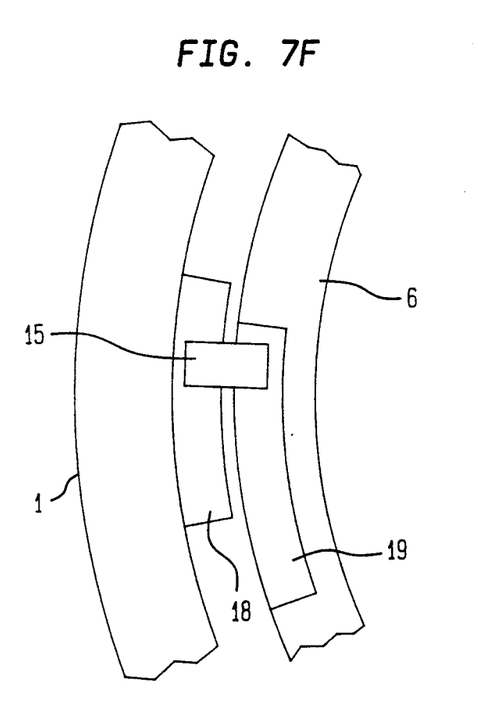

The relationship of tip 5, piston 6, and cam 18 may be most easily understood by reference to FIG. 7F which shows that tip 15 extends across both cam 18 and piston 6 such that as tip 15 advances through the cycle illustrated in FIGS. 7A through 7D, tip 15 presses on piston 6 and is similarly acted on by cam 18, attached to housing 1. Cam 18 forces tip 15 to traverse the perimeter of cam 18 as it is advanced by button 3 and allowed to return to its extended condition under the influence of spring 14 (FIG. 1). In traversing cam 18, tip 15 is forced to move laterally to the axis of rod 16 shown in FIG. 7E. This lateral movement is allowed by flexure in rod 16 (FIG. 1) which bends to allow tip 15 to deflect around the perimeter of cam 18. The flexure, which operates as a spring, returns tip 15 to a central location in line with the axis of the set link when tip 15 is not within the range of effectiveness of cam 18. Such condition occurs twice, first at the end of the distal travel of tip 15 as seen in FIG. 7C and second at the end of the proximal travel of tip 15 as seen in FIG. 7A.

The set system converts the trocar from the protected state to the operational state. The surgeon is merely required to depress set button 13 to effect this conversion. Housings 1 and 2 are preferably designed to cooperate to provide a handgrip for applying force to the instrument in order to effect a puncture. In the course of applying the required force, set button 13 is automatically depressed to effect conversion to an operational state. It is desirable that subsequent processes indicated in FIG. 2 not be impeded by the maintenance of set button 13 in a depressed condition since this is likely to be the case either incidentally or by design on the part of the surgeon. Processes subsequent to set therefore must proceed properly regardless of whether set button 13 is held in a depressed condition or allowed to return to an extended position under the influence of set link spring 14. This feature will be best understood by reference to FIGS. 7E and 7F.

Piston 6 has thereon a piston return slot 19 which is sufficiently deep to avoid interference with tip 15. Slot 19 is located relative to cam 18 such that the distal movement of tip 15 which accompanies depression of button 13 causes tip 15 to interfere with piston 6 thereby advancing piston 6 towards its latched position as seen in FIGS. 7A through 7D. At the end of the distal travel of tip 15, corresponding to a fully depressed button 13, tip 15 has passed the most distal extent of cam 18 and is free to spring back to a condition where it is in line with the axis of the set system. This lateral motion of tip 15 places tip 15 within slot 19 where it does not interfere with piston 6. Piston 6 is therefore free to return proximally to its protected state location even if tip 15 is maintained in its most distal location. Tip 15 is also free to return to its most proximal location whether piston 6 is in its distal latched or in its proximal released position.

The system for de-latching piston 6 in accordance with the invention and thereby converting the trocar system to a protected state will be described with reference to FIGS. 8A through 8D.

Figure 8A:
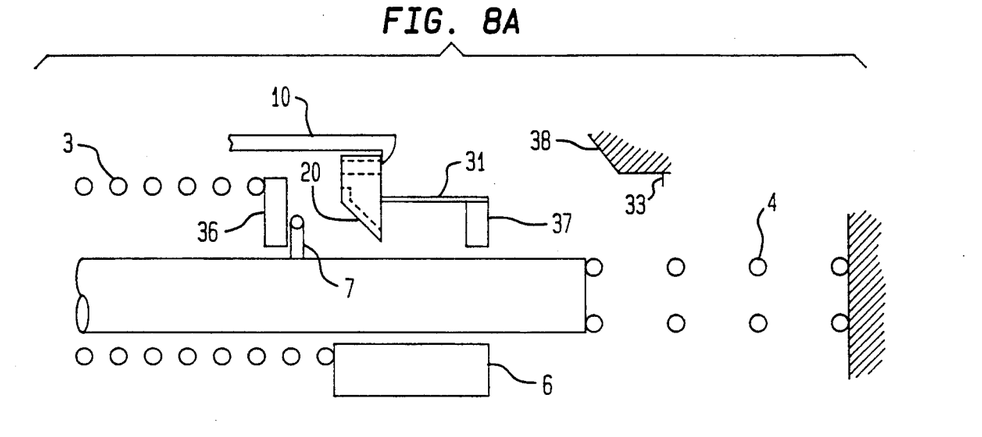
FIGS. 8A through 8D show in sequential diagrammatic views an embodiment of the system for de-latching the piston to allow its retraction into the housing.

The de-latching process comprises two processes referred to above as "arming" and "triggering." FIG. 8A of this sequence corresponds to the operational state. In FIG. 8A, pin 7 is shown pressed against piston slot distal end 36 by spring 4 while element 20 is latched to housing by engagement of edge 25 against link 10. Piston 6 is urged proximally in this state by spring 3. Flex cam support 31 serves to springably attach element 20 to piston 6.

Figure 8B:
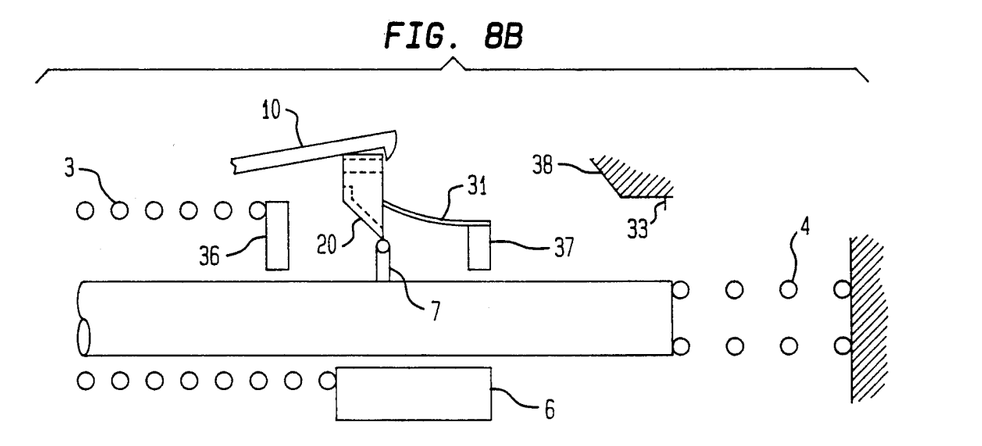
Figure 8C:
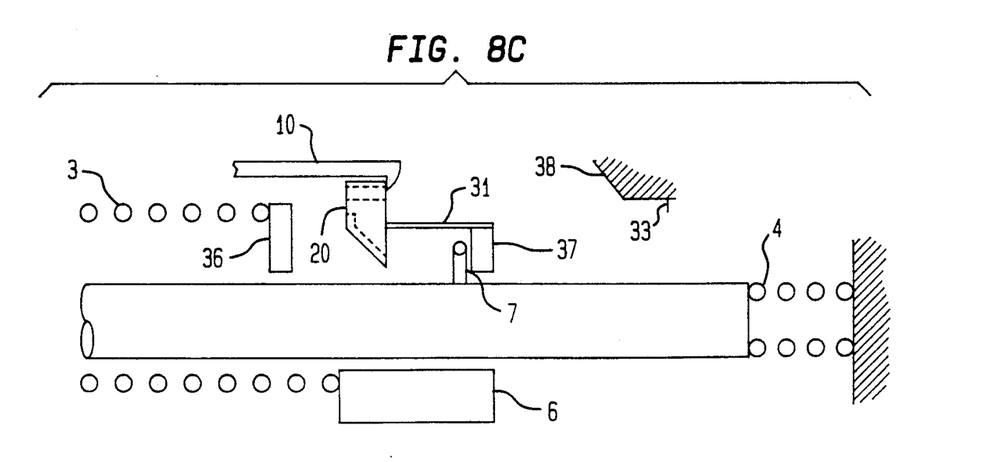

The arming process is illustrated in FIGS. 8B and 8C where pin 7 is moved proximally as stylet 5 is urged proximally by a force applied to tip 17. In these Figs. ramp 27 cams element 20 upward as driver 23 impinges on its surface. FIG. 8C shows pin 7 bearing against the proximal end 37 of piston slot 8 which prevents further retraction of stylet 5 into housing 1.

Figure 8D:
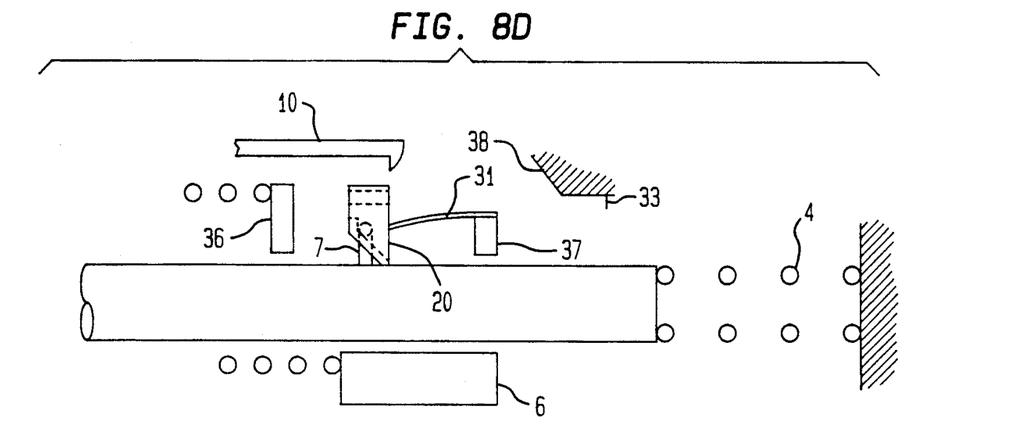
Figure 8E:
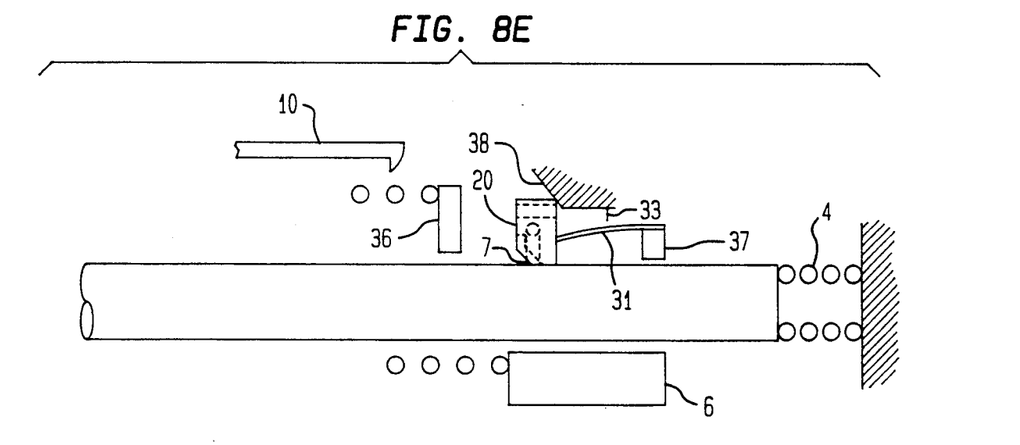
Figure 8F:
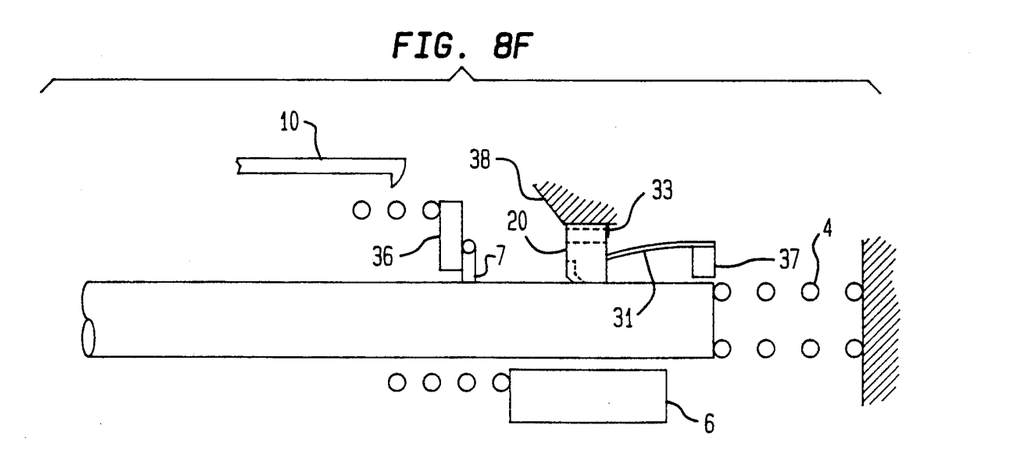

The triggering process is illustrated in FIGS. 8D through 8F where release of force applied to tip 17 allows spring 4 to drive stylet 5 distally. FIG. 8D illustrates the camming down of element 20 by pin 7 to effect the de-latching of element 20 and link 10. In this condition, piston 6 is free to move proximally under the influence of spring 3.

FIG. 8E shows piston 6 partially retracted into housing 1 with element 20 contacting full release cam 38 which is part of housing 1. This contact causes element 20 to be further cammed down to depress element 20 to a level where reset edge 29 falls below the underside of driver 23 allowing driver 23 to ride over and across reset edge 29 thereby freeing driver 23 from contact with ramp stop 30 where it is trapped in order to hold element 20 in the de-latched position to prevent re-latching. After driver 23 rides over edge 29, it is free to move to the distal end of piston slot 8 where, as is seen in FIG. 8F, piston 6 is bearing against stop 33. Spring 4 assures that pin 7 comes to rest against the distal end 36 of piston slot 8 where it remains until piston 6 is advanced again to its latched position shown in FIG. 8A, such action converting the trocar from the protected state shown in FIG. 8F to the operational state of FIG. 3. The armed state is illustrated by FIG. 8C.

Figure 9A:
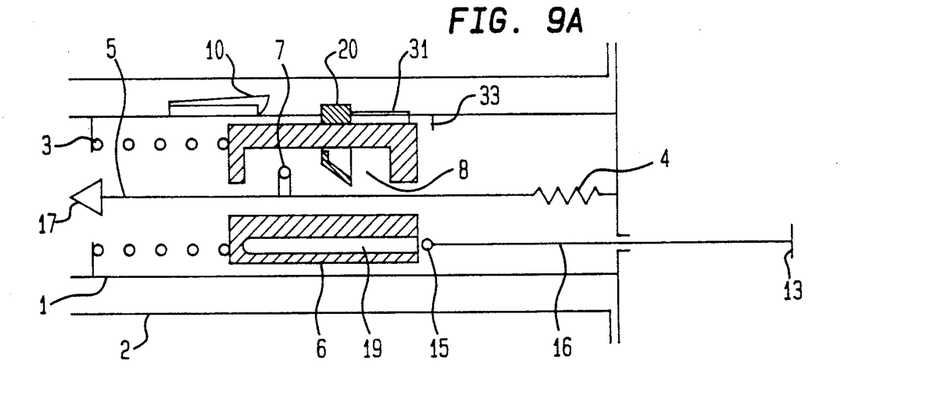
FIGS. 9A through 9F show in sequential diagrammatic views the complete operation of the trocar system.
Figure 9B:
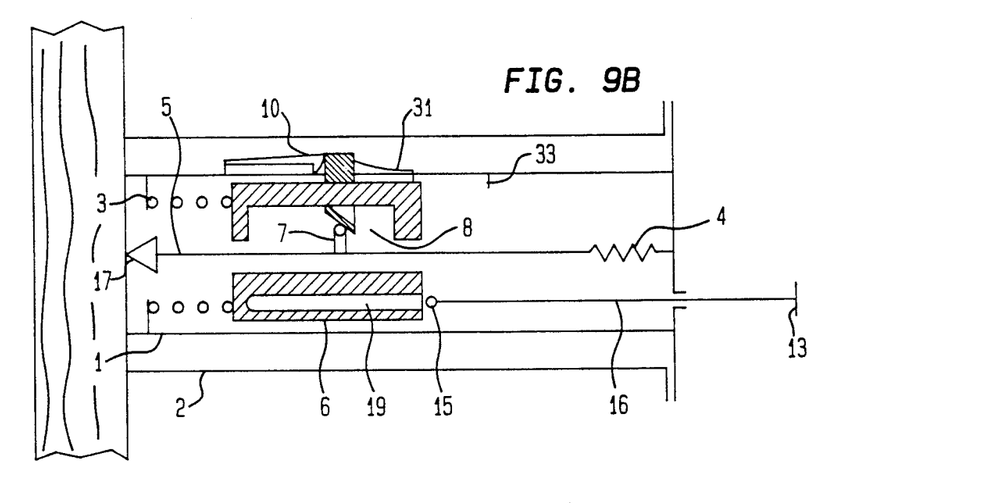

Full operation of the trocar system is illustrated in FIGS. 9A through 9F. FIG. 9A shows the system in the protected state in which it will be received by the surgeon. In FIG. 9B, the trocar system, still in the protected state, is shown pressed against a tissue wall. In this condition, the system is in a state between protected and operational. Flex cam element 20 is cammed upwardly by pin 7 as piston 6 is advanced by set system 34. Stylet 5 is prevented from advancing by stylet tip's 17 pressing against the tissue before it.

Figure 9C:
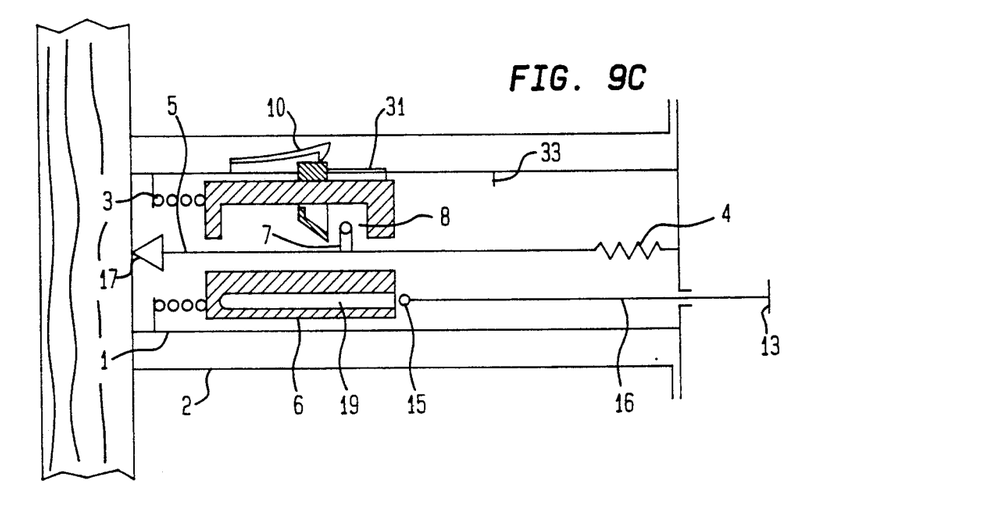

FIG. 9C shows pin 7 having reached the proximal end 37 of piston slot 8. In this condition, further advance of piston 6 is accompanied by an equal advance of stylet 5 driving stylet tip 17 into the tissue. As seen in FIG. 9C, flex cam element 20 cams link 10 up as piston 6 advances.

Figure 9D:
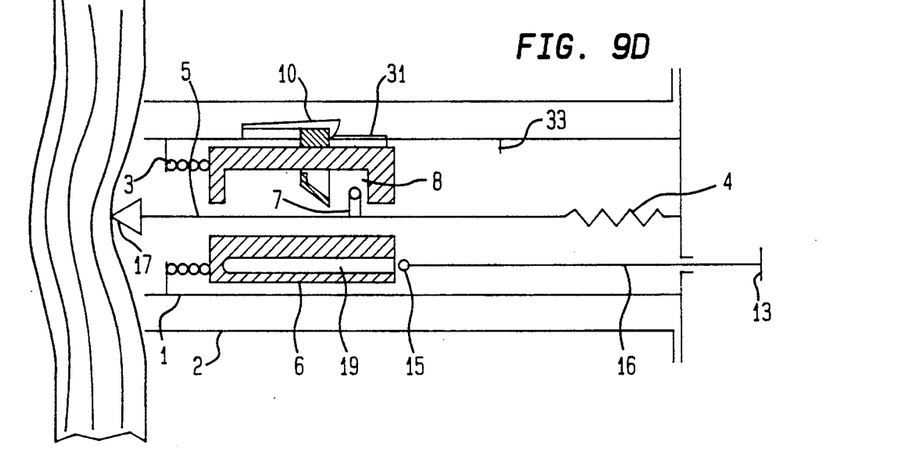
Figure 9E:
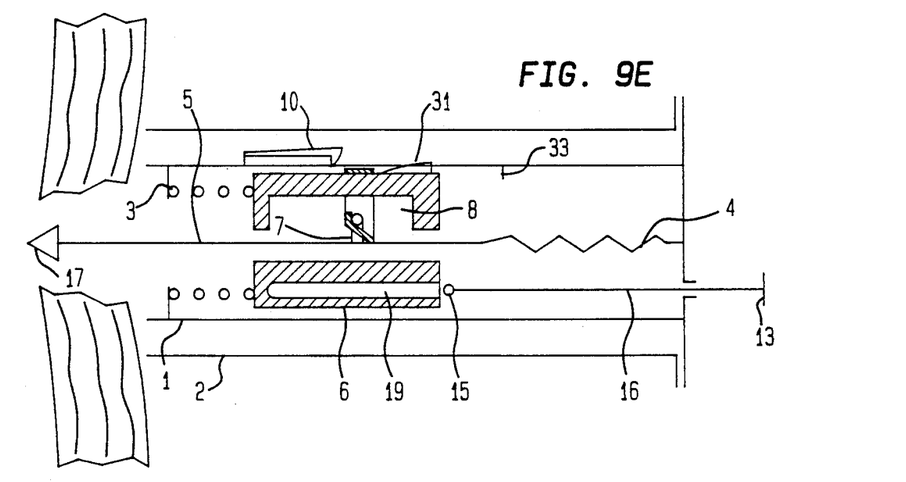

FIG. 9D shows the system in the armed state where stylet 5 is extended and partially piercing the surface of the tissue wall with stylet pin 7 bearing on the proximal end of slot 8. FIG. 9E illustrates a transient condition where tip 17 has fully penetrated the tissue wall and has partially extended distally under the influence of spring 4 with pin 7 having cammed down element 20 to a point where abutment edge 25 has been de-latched from the restraining lip of link 10 and pin 7 has come to rest against ramp stop 30 which thereby prevents re-latching of element 20 and link 10.

Figure 9F:
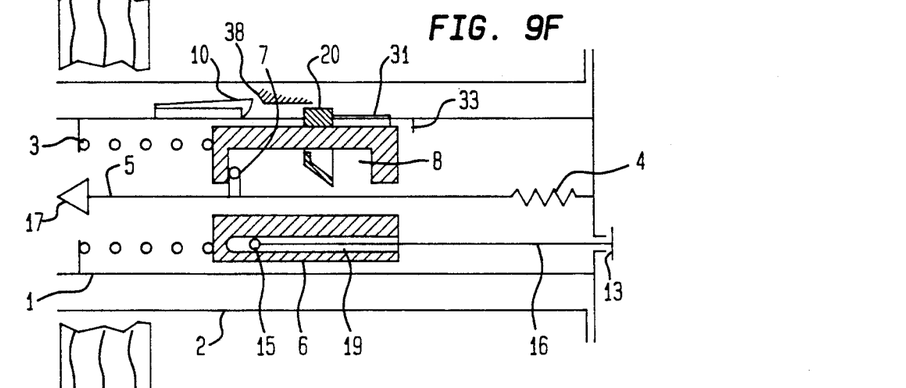

FIG. 9F shows the protected state with element 20 fully cammed down by 38, which releases pin 7, as well as pin 7 bearing against the distal end of piston slot 8. Piston return slot 19 is shown straddling set link tip 15. The trocar system, including cannula 9 of housing 2 is shown fully protruding through the tissue wall. In this condition the trocar can be withdrawn proximally from its location within the system, leaving cannula 9 of housing 2 in place within the puncture hole where it may be used to pass instruments into the body cavity.

As the trocar is withdrawn from housing 2, flap valve 12 which is urged toward the axis of housing 2 by a suitable spring element, comes to rest against the face of O-ring 11, effectively sealing the aperture in housing 2 through which housing 1 is introduced into housing 2. This seal prevents the leakage of fluids from the body cavity. O-ring 11 also serves to seal the housing 2 aperture when housing 1 is in place in housing 2 by radially pressing against the cylindrical outer surface of housing 1.

Figure 10:
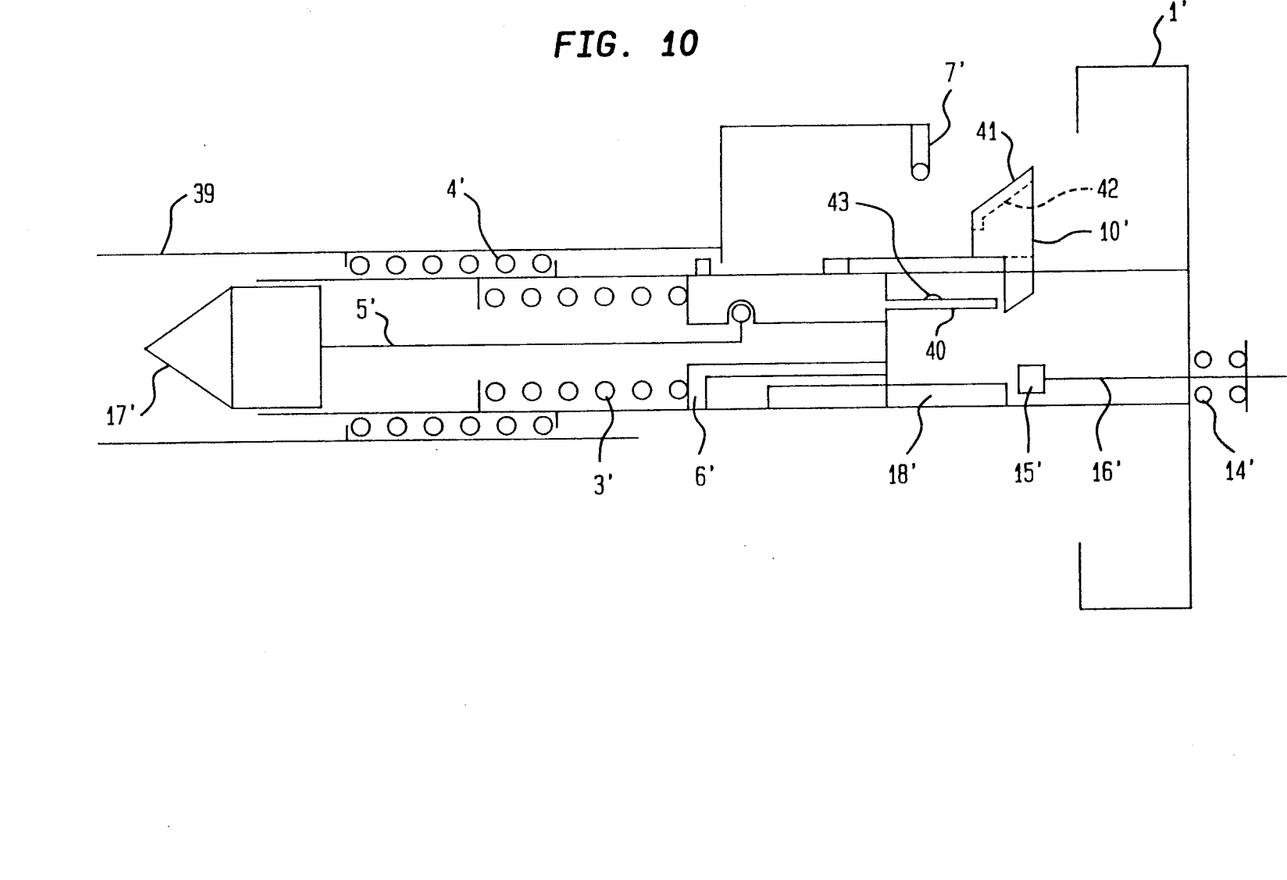
FIG. 10 shows an alternative embodiment.

FIG. 10 is an alternative embodiment of a trocar in accordance with the invention. In this embodiment a trocar similar to the embodiment of FIG. 1 also includes a distally-biased tubular slideable retractable tissue displacement sensor which responds to the displacement of tissue by the stylet point by retracting proximally. In FIG. 10, elements which are similar to those of the embodiment of FIG. 1 are labeled with the same number with the addition of a prime in order to stress the similarity between the two devices. Also illustrative figures have been omitted as being unnecessary where the figures showing the first embodiment also apply to the embodiment of FIG. 10. Such Figures include the trocar being shown inserted into the second housing of FIG. 1, the sequence of states and processes of FIG. 4, the puncturing process illustrated in FIG. 6, and the piston reset system shown in FIG. 7.

Other figures also apply, although not identically. These include FIG. 5, with the sensor travel in place of stylet travel, FIG. 8 showing pin 7' attached to the tubular sensor as described below and FIG. 9 with the modification described below.

This alternative embodiment includes a trocar housing 1' which may be slideably disposed within an outer housing (not shown in FIG. 10) which may be as is illustrated at 2 of FIG. 1. Return spring 3' is arranged against an abutment edge of housing 1'. Tubular sensor 39 is shown extending distally beyond the pointed end of stylet 5'. It will be understood that the tissue displacement sensor need not be tubular nor does it need to encircle the stylet tip 17'. It will be appreciated that this protective housing or shield may be an extension of the trocar housing as shown in FIG. 10 or it may be alternatively the cannula section of the first housing illustrated at 9 of FIG. 1 and that the end of the sensor is not required to extend beyond the distal-most end of the stylet 5' in the set condition. Second spring 4' is connected between the trocar housing 1' and tubular shield 39 to exert a distally biasing force on shield 39 and force the edge of shield 39 to press against an edge of trocar housing 1' to prevent further distal travel of shield 39 and to establish a "home" reference location of sensor 39 relative to housing 1'. The other end of spring 3' is fitted against piston 6' which is slideably mounted within housing 1. In this embodiment pin 7' is mounted on sensor 39.

Stylet 5' is connected to piston 6' through an extension of 5' which enters into a tight-fitting slot on piston 6'. It will be understood that other ways of connecting stylet 5' to piston 6' will occur to those skilled in the art. The two separate parts may also be fabricated as a single part.

Retention link 10', shown flexibly attached to housing 1', carries a lip for latching and restraining movement of piston 6' through its engagement with piston flex lip 40 and an upper cam ramp 41 and a lower cam ramp 42 which interact with pin 7' as sensor 39 moves first proximally and then distally to effect delatching of piston 6' from link 10'. It should be understood that cam ramp 41 and cam ramp 42 function much the same as the corresponding ramps 26 and 27 shown in FIG. 3.

The other elements of FIG. 3, including ramp stop 30' and reset edge 29' seen in FIG. 10, provide essentially the same function as described in connection with the embodiment of FIG. 1, namely maintenance of the de-latched condition until piston 6' has moved to a point where inadvertent re-latching is not possible. The final lifting of link 10' which is required to enable pin 7' to clear reset edge 29' and thereby allow sensor 39 to return to its home location, is provided by cam bump 43 disposed on lip 40 which cams link 10' upward as piston 6' moves proximally by spring 3'.

The principle of operation of this embodiment is substantially identical to that of the first described embodiment, that is, using the decrease of resistance which is experienced as the trocar completes passage through the body cavity wall to initiate a mechanically implemented, automatic process of de-latching a proximally biased piston which is operative to carry the stylet with it as the piston retracts proximally within the protective housing.

In the protected position, slideable sensor 39 extends beyond the pointed end of stylet 5' for the purpose of sensing displacement of tissue by the end of stylet 5'. As the end of the sensor 39 is forced against tissue it retracts. As the shield 39 retracts, pin 7', similar to stylet pin 7 shown in FIG. 2, which is mounted on the inner surface of tubular sensor 39, engages the upper ramp surface 41 of retaining link 10, similar to link 10 of FIG. 1, thereby flexing the retaining link 10' downward to allow pin 7' to retract proximally with the sensor 39. The sensor 39 is biased by spring 4' in the distal direction such that when the trocar pierces the body cavity wall and the sensor 39 is free to move it will do so. In so doing, pin 7' engages the second lower ramp surface 42 of the retaining link 10' thereby flexing it upward and causing the retaining link to disengage from piston 6' to which the stylet 5' is attached. The piston 6' is biased proximally by spring 4' such that when piston 6' disengages from the retaining link 10', it moves proximally thereby retracting the stylet 5' within the protective housing and preventing further inadvertent contact of the stylet point with tissue.

It will now be appreciated that a common feature of these two embodiments is that a distally-biased element which carries an engaging pin and which is forced to move proximally by the tissue resistance experienced as the trocar is forced to puncture a body cavity wall, automatically moves to its original distal location after the tip of the trocar has completely passed through the wall. This sequence of movements, first proximal and then distal, automatically first arms and then triggers a de-latching mechanism which enables a proximally acting biasing element to retract the pointed stylet into a protective housing. The trocar may be re-set from a protected to an operational state in the manner illustrated in FIG. 7.

What is claimed is:

1. A trocar comprising:
a trocar housing, said trocar housing having a proximal end and a distal end;
a piston slideably mounted in the housing and reciprocable therein;
a stylet having a distal end and a sharp tip at said distal end;
cooperating means on said piston and said stylet for restraining said stylet for limited movement with respect to said piston;
means operatively connected to said trocar housing for biasing the piston in a direction toward the proximal end of the trocar housing;
latching means disposed in the trocar housing for latching the piston against movement in the proximal direction; and
de-latching means operatively connected to the piston and responsive to movement of the stylet relative to the piston to allow movement of the piston in the proximal direction.

2. The trocar of claim 1 further comprising setting means for moving the piston into position for latching.

3. The trocar of claim 1 wherein said latching means comprises a retention link located in said trocar housing and a corresponding latch on the piston which are engaged whenever the piston is moved into position for latching.

4. The trocar of claim 1 wherein said cooperating means comprises a pin on said stylet and a slot on said piston, said pin slideably engaging the slot on said piston.

5. The trocar of claim 4 wherein movement of the stylet toward the distal end of the housing causes the pin on said stylet to move within the slot on said piston and to engage said de-latching means for operation thereof.

6. The trocar of claim 1 further comprising a spring for biasing the stylet in the direction of the distal end of the housing.

7. The trocar of claim 1 wherein the de-latching means is a flex cam element flexibly attached to said piston, said cam element including at one end thereof an abutting edge for engaging the latch means and further comprising a cam surface at an opposing end thereof for engaging said pin on said stylet, said engagement effecting movement of the cam element so as to move the abutting edge from engagement with said latch means.

8. The trocar of claim 1 further comprising:
a second housing arranged coaxially with said trocar housing to define a handgrip therewith;
a guide tube secured to and extending from said second housing, said trocar housing being mountable longitudinally central within the guide tube;
an O-ring disposed in said second housing against the trocar housing; and
a flap-valve in said second housing springably biased to rest against said O-Ring to thereby seal against fluid passage when the trocar housing is removed from the second housing.

9. A trocar comprising:
a trocar housing having an open distal end;
a stylet located within said trocar housing, said stylet having a sharp tip at a distal end thereof, said stylet being slideably mounted for movement between an extended position and a retracted position, the sharp tip in the retracted position of the stylet being located within a second housing arranged coaxially with said trocar housing, said stylet being disposed longitudinally central within the trocar housing;
a return spring n said trocar housing for biasing said stylet toward said retracted position;
latching means in said trocar housing for locking said stylet in said extended position wherein the sharp tip extends beyond the distal end of the second housing;
de-latching means located within said trocar housing for releasing the latching means to allow the return spring to retract the stylet into the second housing; and a set link slideably mounted in and projecting from said trocar housing operative for moving said stylet form the retracted to the extended position.

10. The trocar of claim 9 wherein the delatching means comprises:
a piston, said piston being slideably mounted within said trocar housing and having a delatching element thereon;
means connecting said stylet and said piston for allowing limited movement between the stylet and the piston;
said piston being connected to said set link and said return spring such that operation of the set link to move the stylet from the retracted to the extended position moves said piston and thereby moves the stylet through said means connecting the stylet and piston, said piston compressing the return spring as the piston moves from the retracted to the extended position.

11. The trocar of claim 10 wherein said latching means comprises said piston having a latch thereon and said trocar housing having a corresponding retention link, said latch engaging said retention link when said piston is moved to the extended position.

12. The trocar of claim 10 wherein said connecting means comprises a pin on said stylet and a slot on said piston, said pin slideably engaging the slot on said piston.

13. The trocar of claim 12 wherein movement of the stylet toward the distal end of the housing causes the pin on said stylet to move within the slot on said piston and to engage said de-latching means for operation thereof.

14. The trocar of claim 10 further comprising a spring for biasing the stylet in the direction of the distal end of the housing.

15. The trocar of claim 10 wherein the de-latching element is a flex cam element flexibly attached to said piston, said cam element including at one end thereof an abutting edge for engaging the latch means and further comprising a cam surface at an opposing end thereof for engaging said pin on said stylet, said engagement effecting movement of the cam element so as to move the abutting edge from engagement with said latch means.

16. A trocar comprising:
a trocar housing having an open distal end;
a stylet located within said trocar housing, said stylet having a sharp tip at a distal end thereof, said stylet being slideably mounted for movement between an extended position and a retracted position, the sharp tip in the retracted position of the stylet being located within a second housing arranged coaxially with the trocar housing, said stylet being disposed longitudinally central within the trocar housing;
a return spring in said trocar housing for biasing said stylet toward said retracted position;
a set link slideably mounted in and projecting from said trocar housing operative for moving said stylet form the retracted to the extended position;
a piston, said piston being slideably mounted within said trocar housing;
a protruding element on said stylet operative for travel within a confining slot in said piston for allowing limited movement between the stylet and the piston;
said piston being connected to said set link and said return spring such that operation of the set link to move the stylet from the retracted to the extended position moves said piston and thereby moves the stylet through said means connecting the stylet and piston, said piston compressing the return spring as the piston moves from the retracted to the extended position;
latching means in said trocar housing for locking said stylet in said extended position wherein the sharp tip extends beyond the distal end of the trocar housing; and
de-latching means located within said trocar housing for releasing the latching means to allow the return spring to retract the stylet into the housing.

17. In a trocar system including a protective housing having a distal end and a proximal end, a stylet, and means for retracting the stylet into the protective housing, the improvement comprising a delatching means and a cooperating distally biased blunt sensor element, said distally biased blunt sensor element retracting proximally and extending distally in a normal cycle of use of the trocar system, the cycle of use, first proximal and then distal, automatically activating said delatching means, and said means for retracting the stylet into said protective housing being enabled when said delatching means is activated.

18. A trocar comprising:
a trocar housing having an open distal end;
a stylet located within said trocar housing, said stylet having a sharp tip at a distal end thereof, said stylet being slideably mounted for movement between an extended position and a retracted position, the sharp tip in the retracted position of the stylet being located within a protecting housing, said stylet being disposed longitudinally central within the trocar housing;
means for retracting the stylet into said trocar housing;
a set link slideably mounted in and projecting from said trocar housing operative for moving said stylet from the retracted to the extended position;
a piston, said piston being slideably mounted within said trocar housing;
said piston being connected to said set link and said return spring such that operation of the set link to move the stylet from the retracted to the extended position moves said piston, said piston compressing the return spring as the piston moves from the retracted to the extended position;
latching means in said trocar housing for locking said stylet in said extended position wherein the sharp tip extends beyond the distal end of the protecting housing;
de-latching means located within said trocar housing for releasing the latching means to allow the return spring to retract the stylet into the housing; and
a cooperating distally biased blunt sensor element, said distally biased sensor element retracting proximally and extending distally in a normal cycle of use of the trocar system, the cycle of use, first proximal and then distal, automatically activating said delatching means, and said means for retracting the stylet into said trocar housing being enabled when said delatching means is activated.

19. A trocar comprising:
a trocar housing having an open distal end;
a stylet located within said trocar housing, said stylet having a sharp tip at a distal end thereof, said stylet being slideably mounted for movement between an extended position and a retracted position, the sharp tip in the retracted position of the stylet being located within a second housing, said stylet being disposed longitudinally central within the trocar housing;

a return spring in said trocar housing for biasing said stylet toward said retracted position;

latching means in said trocar housing for locking said stylet in said extended position wherein the sharp tip extends beyond the distal end of the second housing;

de-latching means located within said trocar housing for releasing the latching means to allow the return spring to retract the stylet into the second housing;

a set link slideably mounted in and projecting from said trocar housing operative for moving said stylet from the retracted to the extended position;

the delatching means comprising:

a piston, said piston being slideably mounted within said trocar housing and having a delatching element thereon;

means connecting said stylet and said piston for allowing limited movement between the stylet and the piston;

said piston being connected to said set link and said return spring such that operation of the set link to move the stylet from the retracted to the extended position moves said piston and thereby moves the stylet through said means connecting the stylet and piston, said piston compressing the return spring as the piston moves from the retracted to the extended position.

* * * * *